US010602934B2

United States Patent
Zaman

(10) Patent No.: US 10,602,934 B2
(45) Date of Patent: Mar. 31, 2020

(54) PROBE FOR DETECTING ATHEROSCLEROSIS

(71) Applicant: The Board of Trustees of the Leland Stanford Junior University, Palo Alto, CA (US)

(72) Inventor: Raiyan Zaman, Palo Alto, CA (US)

(73) Assignee: THE BOARD OF TRUSTEES OF THE LELAND STANFORD JUNIOR UNIVERSITY, Palo Alto, CA (US)

(*) Notice: Subject to any disclaimer, the term of this patent is extended or adjusted under 35 U.S.C. 154(b) by 406 days.

(21) Appl. No.: 15/592,821

(22) Filed: May 11, 2017

(65) Prior Publication Data

US 2017/0325697 A1    Nov. 16, 2017

Related U.S. Application Data

(60) Provisional application No. 62/335,407, filed on May 12, 2016.

(51) Int. Cl.
*A61B 5/02*    (2006.01)
*A61B 6/00*    (2006.01)
(Continued)

(52) U.S. Cl.
CPC ........ *A61B 5/02007* (2013.01); *A61B 1/3137* (2013.01); *A61B 5/004* (2013.01);
(Continued)

(58) Field of Classification Search
CPC ....... A61B 5/02; A61B 1/3137; A61B 6/4417; A61B 6/5247; A61B 5/02007;
(Continued)

(56) References Cited

U.S. PATENT DOCUMENTS

| 7,566,881 B2 * | 7/2009 | Parvin | G01S 7/4802 |
| | | | 250/394 |
| 8,870,770 B2 * | 10/2014 | Dogra | A61B 5/0059 |
| | | | 600/437 |

(Continued)

FOREIGN PATENT DOCUMENTS

WO    WO2012064366    5/2012

OTHER PUBLICATIONS

Zabihian "In vivo dual-modality photoacoustic and optical coherence tomography imaging of human dermatological pathologies" published Jul. 31, 2015, Biomedical Optics Express 3163 (Year: 2015).*

(Continued)

*Primary Examiner* — Oommen Jacob
(74) *Attorney, Agent, or Firm* — Merchant & Gould P.C.

(57) ABSTRACT

A probe device for detecting atherosclerotic plaque may include: an elongate shaft having a proximal end for coupling with a catheter and a distal end; an opening in a side of the shaft; a scintillating window disposed over the opening to form a water tight seal and thus form an imaging window compartment; a 45-degree rotating mirror disposed at least partially within the imaging window compartment; and an ultrasound transducer disposed at least partially within the imaging window compartment. The probe is a dual-modality, catheter radionuclide imaging and photoacoustic tomography (CRI-PAT) probe.

15 Claims, 10 Drawing Sheets

(51) Int. Cl.
*A61B 1/313* (2006.01)
*A61B 5/00* (2006.01)
*A61B 6/03* (2006.01)

(52) U.S. Cl.
CPC .......... *A61B 5/0035* (2013.01); *A61B 5/0095* (2013.01); *A61B 5/6852* (2013.01); *A61B 6/425* (2013.01); *A61B 6/4258* (2013.01); *A61B 6/4417* (2013.01); *A61B 6/504* (2013.01); *A61B 6/5247* (2013.01); *A61B 5/0062* (2013.01); *A61B 5/0084* (2013.01); *A61B 6/03* (2013.01); *A61B 6/037* (2013.01); *A61B 6/4057* (2013.01); *A61B 6/481* (2013.01)

(58) Field of Classification Search
CPC ..... A61B 5/0095; A61B 5/004; A61B 5/0035; A61B 5/6852; A61B 6/425; A61B 6/4258; A61B 6/504; A61B 5/0084; A61B 6/4057; A61B 6/03; A61B 6/037; A61B 6/481; A61B 5/0062
USPC ........................................................ 600/407
See application file for complete search history.

(56) References Cited

U.S. PATENT DOCUMENTS

| | | | | |
|---|---|---|---|---|
| 9,587,976 B2* | 3/2017 | Wang | ................ | G01N 29/2418 |
| 10,105,062 B2* | 10/2018 | Wang | ................ | A61B 5/0062 |
| 2006/0106306 A1* | 5/2006 | Essner | ................ | A61B 8/0833 |
| | | | | 600/436 |
| 2006/0184042 A1* | 8/2006 | Wang | ................ | A61B 5/0073 |
| | | | | 600/476 |
| 2008/0262359 A1* | 10/2008 | Tearney | ............ | A61B 1/00096 |
| | | | | 600/476 |
| 2009/0203991 A1* | 8/2009 | Papaioannou | ....... | A61B 5/0066 |
| | | | | 600/421 |
| 2010/0219348 A1* | 9/2010 | Peter | ................ | A61B 5/0073 |
| | | | | 250/363.04 |
| 2011/0021924 A1* | 1/2011 | Sethuraman | ........ | A61B 5/0095 |
| | | | | 600/463 |
| 2011/0040176 A1* | 2/2011 | Razansky | ........... | A61B 5/0095 |
| | | | | 600/425 |
| 2011/0098572 A1* | 4/2011 | Chen | .................... | A61B 5/0062 |
| | | | | 600/463 |
| 2012/0323112 A1* | 12/2012 | Jokerst | ................ | A61K 49/225 |
| | | | | 600/420 |
| 2014/0276018 A1 | 9/2014 | Mukdadi | | |
| 2014/0303476 A1* | 10/2014 | Dogra | ................ | A61B 5/0084 |
| | | | | 600/407 |
| 2014/0357997 A1* | 12/2014 | Hartmann | ............... | A61B 8/12 |
| | | | | 600/439 |
| 2015/0351722 A1* | 12/2015 | Chen | .................... | A61B 8/485 |
| | | | | 600/427 |
| 2016/0113622 A1* | 4/2016 | Kim | .................... | A61B 8/4416 |
| | | | | 600/466 |
| 2016/0242737 A1* | 8/2016 | Zhou | ........................ | A61B 1/05 |
| 2017/0049518 A1* | 2/2017 | Sinusas | ................. | A61B 34/20 |
| 2017/0325697 A1* | 11/2017 | Zaman | ................ | A61B 1/3137 |

OTHER PUBLICATIONS

Hasegawa "Dual-Modality Imaging of Cancer with SPECT/CT" Technology in Cancer Research & Treatment, ISSN 1533-0346, vol. 1, No. 6, Dec. 2002 (Year: 2002).*

Yoo "Intra-arterial catheter for simultaneous microstructural and molecular imaging in vivo", Nature medicine • Nov. 2011 (Year: 2011).*

Decusatis "Fiber optic Essentials" p. 184, 2005 (Year: 2005).*

Zaman "Fiber-Optic System for Dual-Modality Imaging of Glucose Probes 18F-FDG and 6-NBDG in Atherosclerotic Plaques", PLoS ONE • Sep. 2014 (Year: 2014).*

Cao et al., "High-sensitivity intravascular photoacoustic imaging of lipid-laden plaque with a collinear catheter design," Sci Rep., 6:25236. doi: 10.1038/srep25236, Apr. 28, 2016.

International Search Report and Written Opinion for PCT/US2017/032237, dated Sep. 1, 2017, 16 pages.

Jansen et al., "Intravascular photoacoustic imaging: a new tool for vulnerable plaque identification," Ultrasound Med Biol, 40(6):1037-1048, Epub Mar. 14, 2014.

Zaman et al., "Scintillating balloon-enabled fiber-optic system for radionuclide imaging of atherosclerotic plaques," J Nucl Med., 56(5):771-777, Epub Apr. 9, 2015.

* cited by examiner

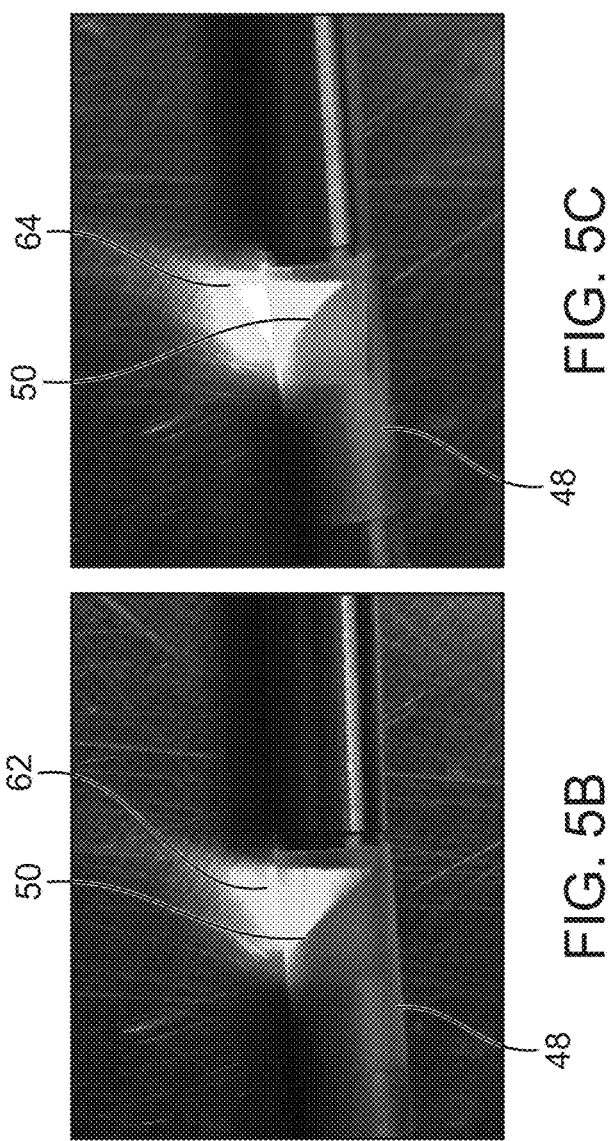

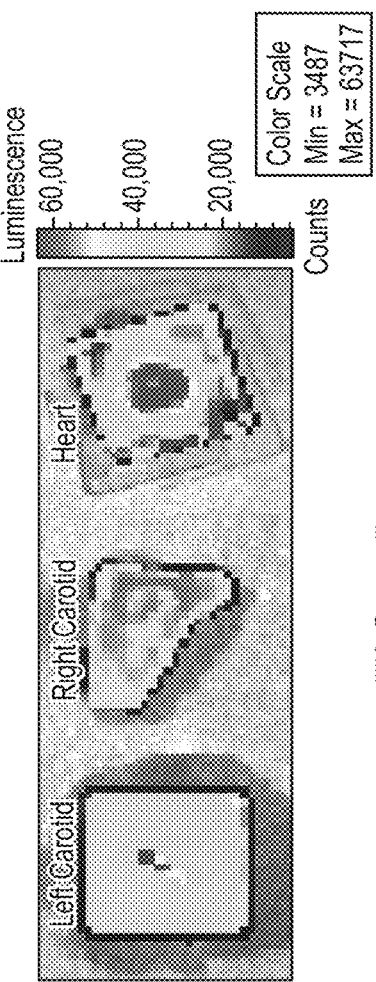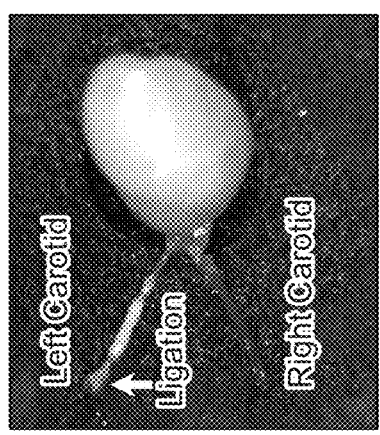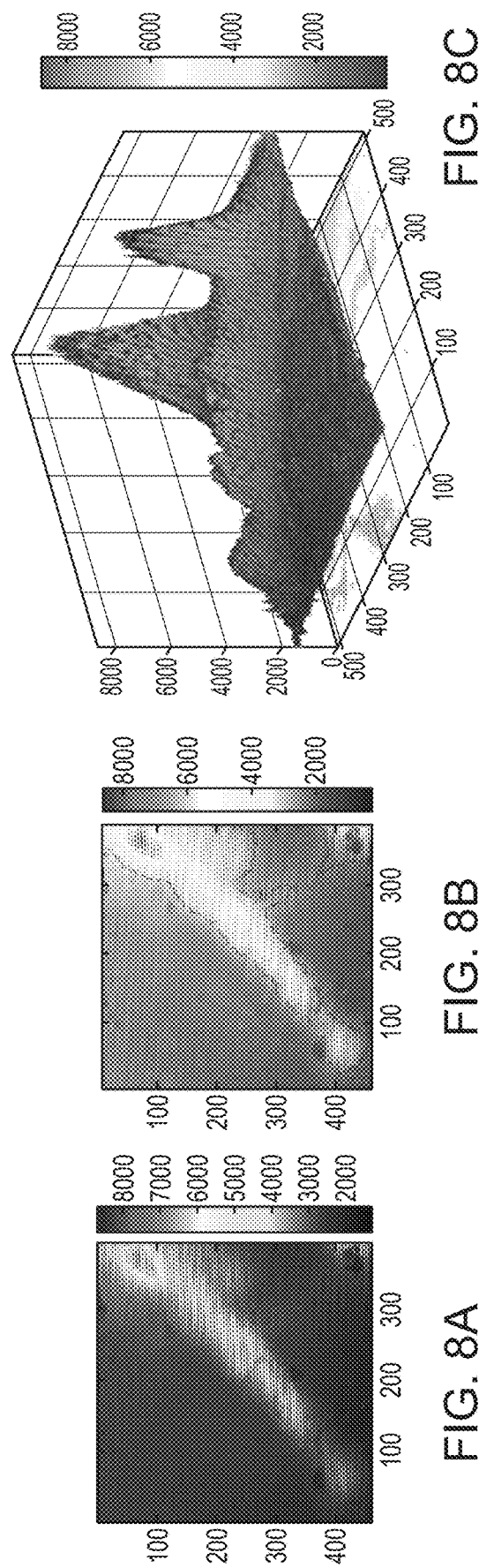

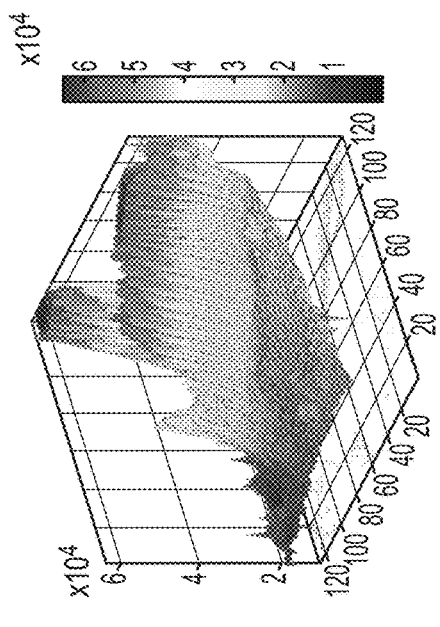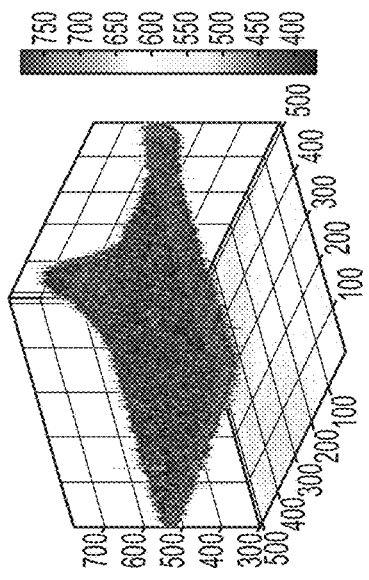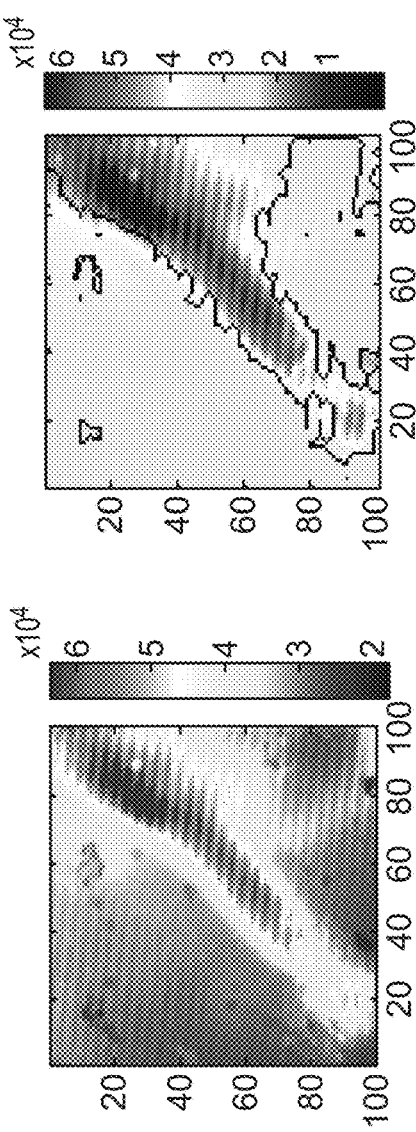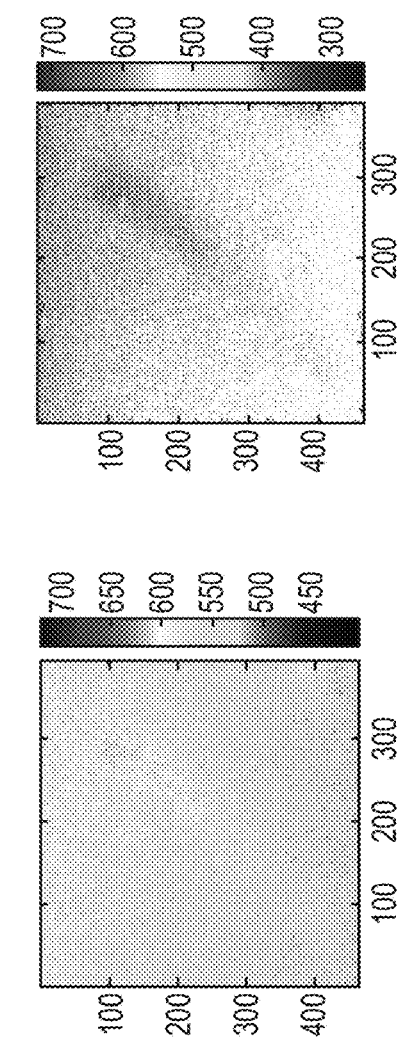

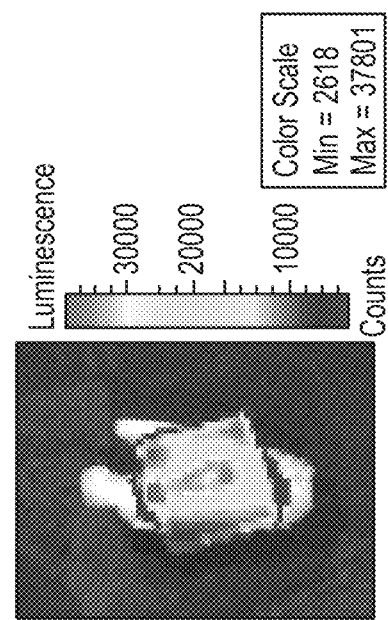
FIG. 13B
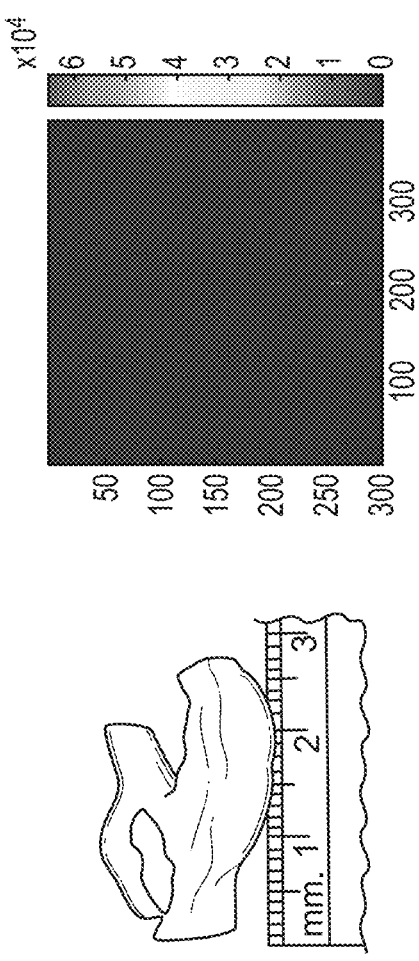
FIG. 13A
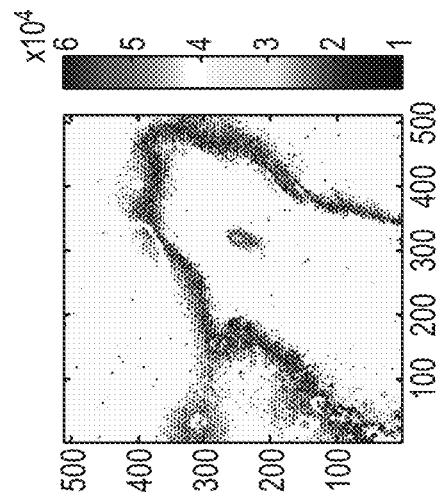
FIG. 13C
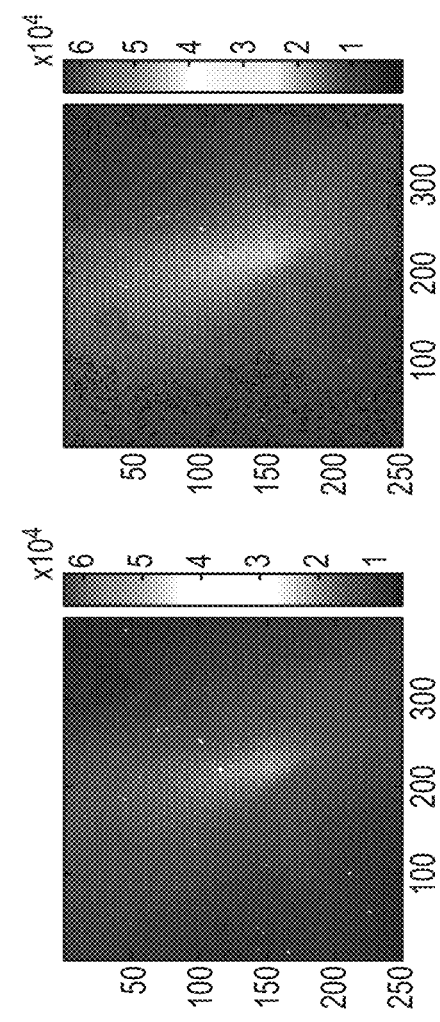
FIG. 14A / FIG. 14B / FIG. 14C

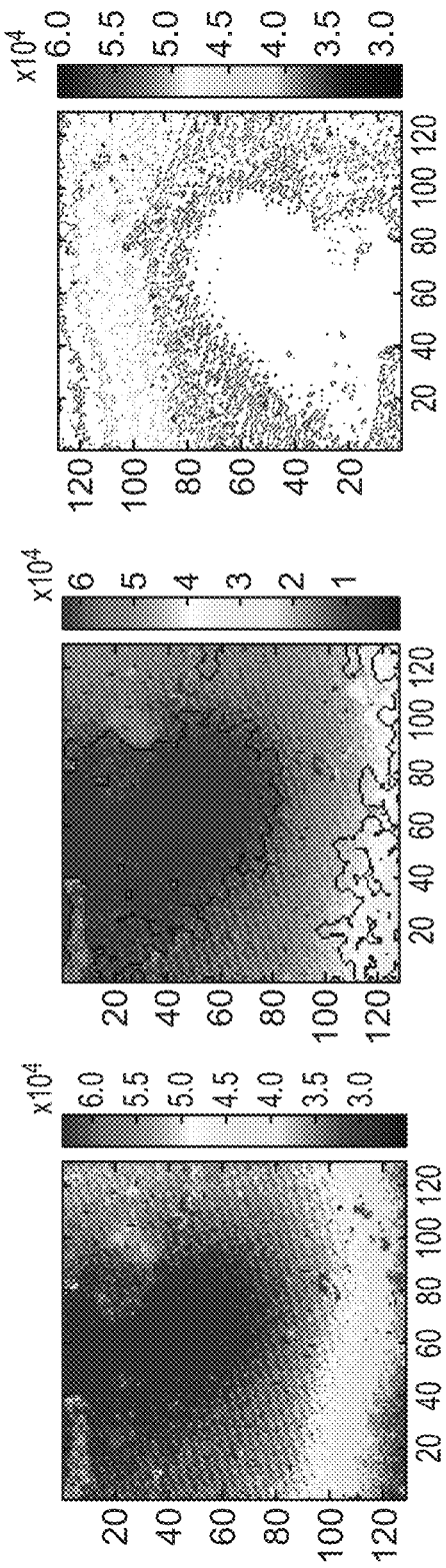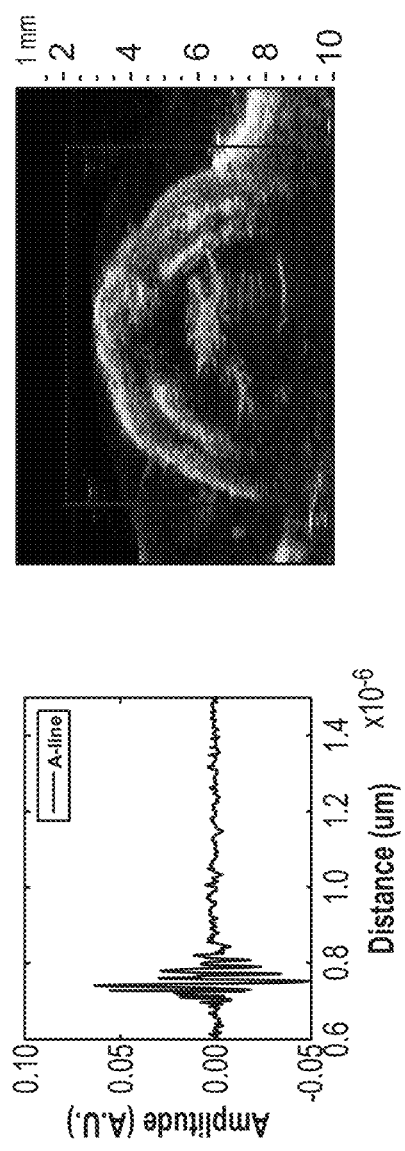

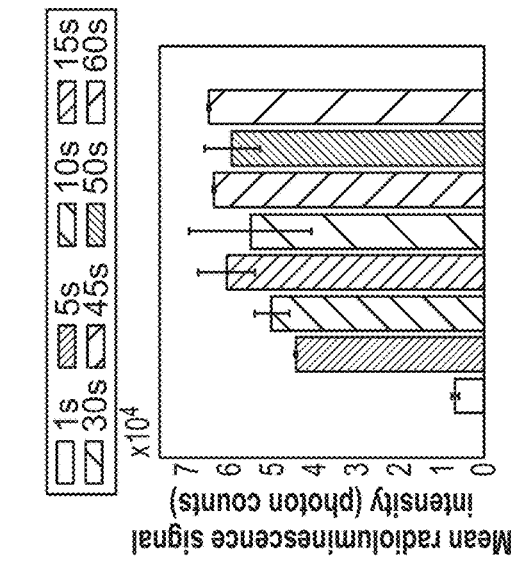
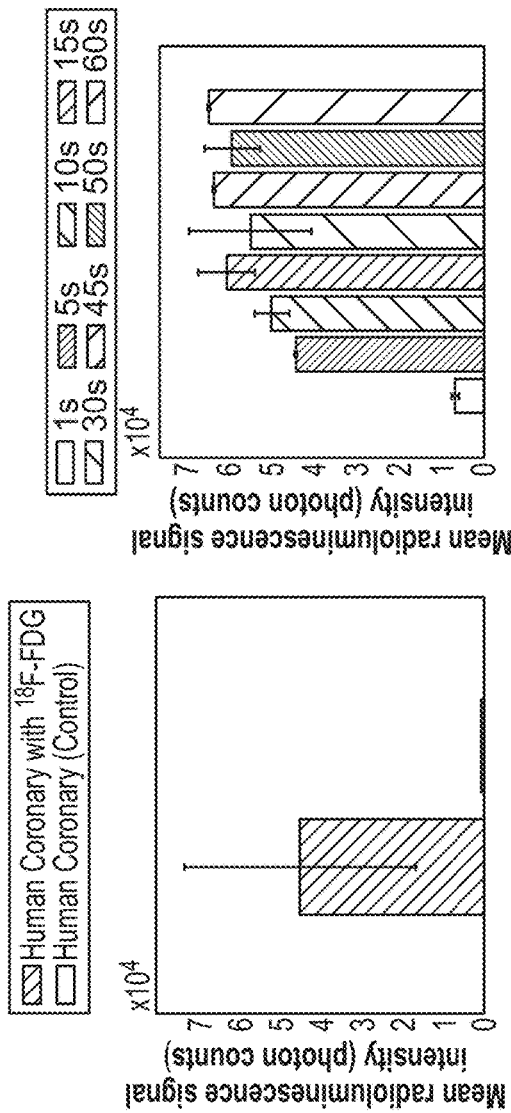
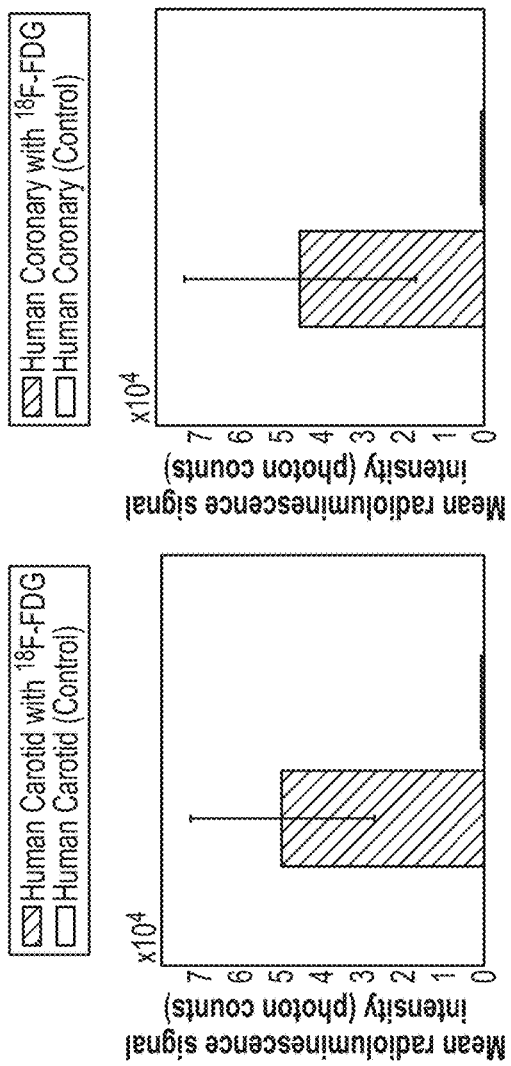
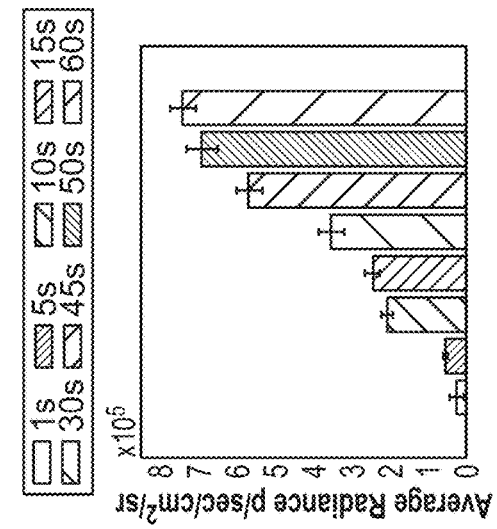
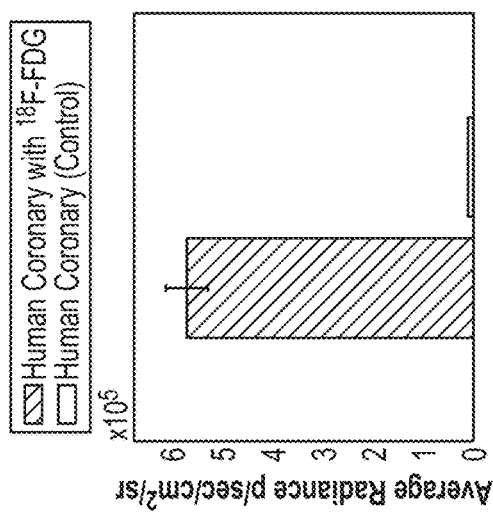
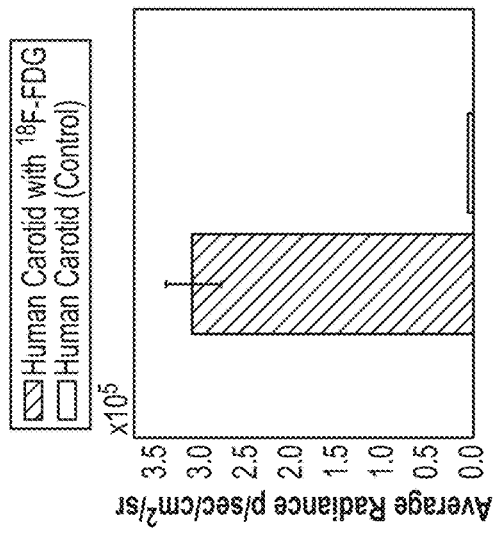

PROBE FOR DETECTING ATHEROSCLEROSIS

CROSS-REFERENCE TO RELATED APPLICATIONS

This application claims the benefit of U.S. Provisional Patent Application No. 62/335,407, filed May 12, 2016, entitled, "Probe for Detecting Atherosclerosis." The disclosure of this priority application is hereby incorporated by reference in its entirety into the present application.

This invention was made with Government support under contract HL127180 awarded by the National Institutes of Health. The Government has certain rights in the invention.

FIELD

The present application relates to medical devices and methods. More specifically, the application relates to a probe device and method for detecting atherosclerosis in blood vessels.

BACKGROUND

Atherosclerosis is a disease in which plaque builds up inside arteries. Atherosclerosis is the usual cause of heart attacks, strokes, and peripheral vascular disease—together called "cardiovascular disease." Cardiovascular disease is the leading cause of death in the United States and worldwide. Atherosclerosis can affect any artery in the body, including arteries in the heart, brain, arms, legs, pelvis, and kidneys. As a result, atherosclerosis may cause many different diseases, based on which arteries are affected. One of the most common forms of atherosclerosis, and the one that causes the most deaths, is atherosclerosis of the coronary arteries, which supply the heart with blood—referred to as "coronary artery disease" or "CAD."

Detection of coronary atherosclerosis is challenging, due to the small size of the coronary arteries, the motion of the beating heart, and obscuring signals from adjacent myocardial (heart muscle) tissue. The current gold standard for detecting CAD, and the procedure used most often, is cardiac catheterization angiography. Cardiac catheterization with angiography involves inserting a thin, flexible catheter into an artery in the leg or arm, advancing the catheter through the artery to one of the coronary arteries, and taking radiographic pictures of the coronary artery (angiography). Blockages in the coronary artery (or arteries) are visible on a live X-ray screen.

One of the shortcomings of cardiac catheterization with angiography is that it only reveals the outlines of the flow space inside the coronary arteries with narrowed (stenotic) arterial segments or blockages. It does not provide any additional information about the atherosclerotic plaque, such as the extent, content, and biology of the plaque. Another shortcoming is that cardiac catheterization with angiography cannot detect early atherosclerotic plaque, which builds up inside the arterial wall but does not yet protrude into the arterial lumen. Thus, it would be beneficial to have improved devices and methods for detecting atherosclerosis in coronary arteries and/or other arteries in the body.

BRIEF SUMMARY

The probe device and method described in this application seek to provide for improved atherosclerosis detection and evaluation, even in early atherosclerosis. A dual-modality, scintillator catheter probe is described herein, with the two imaging modes of the probe being catheter radionuclide imaging ("CRI") and photoacoustic tomography ("PAT"). This dual-modality probe may thus be referred to as a CRI-PAT probe, and the system it is used with may be referred to as a CRI-PAT imaging system. The probe uses 18F-fluorodeoxyglucose (18F-FDG), a marker of vascular inflammation, to detect and characterize atherosclerotic plaque. Compared to currently available plaque detection techniques, the probe and imaging system described herein provide improved sensitivity and resolution of plaque imaging. The probe and imaging system are also able to outline the location of a vulnerable plaque and characterize the plaque by identifying constituents and characteristics of the diseased (plaque) tissue. In other words, the probe and imaging system described herein are not only capable of distinguishing vulnerable plaque from stable plaque, but they can also outline the location of the plaque, using information as to the diseased tissue constituents and characteristics, such as lipid and fatty acid, calcium, elastin, elastic, collagen, and tissue thickness.

In one aspect of the disclosure, a probe device for detecting atherosclerotic plaque in an artery may include: an elongate hollow shaft, having a proximal end for coupling with a catheter and a distal end; an opening in a side of the shaft; a scintillating window disposed over the opening to form a watertight seal and thus form an imaging window compartment in the shaft; a 45-degree rotating mirror disposed at least partially within the imaging window compartment in the shaft; and an ultrasound transducer disposed at least partially within the imaging window compartment in the shaft. In some embodiments, the probe device may further include a leached imaging bundle extending through a central bore of the ultrasound transducer and a multimode fiber extending through the central bore of the ultrasound transducer. The probe may also include a mechanical micromotor extending through the shaft and coupled with the rotating mirror. In some embodiments, the probe also includes at least one micro-magnet connecting the micromotor with the rotating mirror. The probe may also include a spacer for preventing water from flowing from the imaging window compartment to a micro-motor holding compartment in the shaft where the micro-motor is located. In some embodiments, for example, the leached imaging bundle may be an 18,000-pixel leached image fiber. Optionally, the probe device may also include deionized water disposed within the imaging window compartment. The probe device may be a catheter radionuclide imaging and photoacoustic tomography (CRI-PAT) probe, according to one embodiment.

In another aspect of the present application, a system for detecting atherosclerotic plaque in an artery may include a catheter radionuclide imaging and photoacoustic tomography (CRI-PAT) probe and at least one component coupled with the CRI-PAT probe and configured to provide power to at least one of a catheter radionuclide modality or a photoacoustic tomography modality of the CRI-PAT probe. Examples of the component include but are not limited to a laser power supply, a control box, a pulse signal generator, a tunable laser, a microscope objective, a 4-channel delay generator, a pulser-receiver, a digital storage oscilloscope, a computer, a lens, a CCD camera, a liquid circulator and a digital servo-driver. The CRI-PAT probe any of the features described above.

In another aspect of the present disclosure, a method for detecting atherosclerotic plaque in an artery may involve: injecting 18F-fluorodeoxyglucose (18F-FDG) into the artery; advancing a catheter radionuclide imaging and photoacoustic tomography (CRI-PAT) probe into the artery; detecting optical radiation from the atherosclerotic plaque through a scintillating window on the CRI-PAT probe, with one or more optical fibers in the CRI-PAT probe; emitting laser light circumferentially around an inner wall of the artery with a laser and a 45-degree rotating mirror in the CRI-PAT probe; and detecting an acoustic pressure wave from the atherosclerotic plaque in response to the emitted laser light, using an ultrasound transducer located inside the scintillating window of the CRI-PAT probe.

Optionally, the method may further involve identifying the atherosclerotic plaque as a vulnerable plaque, using the detected optical radiation from the atherosclerotic plaque. The method may also involve identifying multiple constituents of the atherosclerotic plaque, based on the detected acoustic pressure wave. The method may also involve providing a first image of the atherosclerotic plaque. For example, providing the first image may involve superimposing the first image on a second image of an artery in which the atherosclerotic plaque resides. The second image of the artery, for example, may be an ultrasound image. Emitting the laser light may involve emitting pulsed laser light.

These and other aspects and embodiments will be described in greater detail below, in reference to the attached drawing figures.

BRIEF DESCRIPTION OF THE DRAWINGS

FIGS. 5A-5C are side views of a portion of the probe of FIGS. 1-3, specifically the scintillating window (FIG. 5A), tunable laser light being delivered through the water-coupled scintillating window at 540 and 560 nm wavelength (green band, FIG. 5B), and (c) tunable laser light being delivered through the water-coupled scintillating window at 1180, 1210, and 1235 nm wavelength (blue band, FIG. 5C);

FIGS. 7A and 7B are: (FIG. 7A) an image of ex vivo murine carotid arteries, one hour after 18F-FDG IV injection of 200 where ligated left and non-ligated right carotid (negative control) arteries are still attached to the heart (positive control), immediately after the organ was harvested for imaging; and (FIG. 7B) radioluminescence signal verification with IVIS-200 imaging system to illustrate the glucose uptake by macrophages in atherosclerotic plaque;

FIGS. 8A-8C are: (FIG. 8A) a CRI image of the ligated left carotid artery of FIGS. 7A and 7B, showing a high radioluminescence signal at the atherosclerotic plaque (exposure time was 45 seconds with binning 1×1 at 50 MHz EM gain); (FIG. 8B) the CRI image showing an outline of the atherosclerotic plaque, using edge detection software according to one embodiment; and (FIG. 8C) a topographical image highlighting the distribution of the radioluminescence signal intensity using contour detection software according to one embodiment;

FIGS. 9A-9C are: (FIG. 9A) a CRI image of the same ligated left carotid artery of FIGS. 7A and 7B, showing a high radioluminescence signal at the atherosclerotic plaque (exposure time was 45 seconds with binning 4×4 at 50 MHz EM gain); (FIG. 9B) the CRI image showing an outline of the atherosclerotic plaque, using edge detection software according to one embodiment; and (FIG. 9C) a topographical image highlighting the distribution of the radioluminescence signal intensity using contour detection software according to one embodiment;

FIGS. 10A-10C are: (FIG. 10A) a CRI image of the same right carotid artery of FIGS. 7A and 7B, where exposure time was 45 seconds with binning 4×4 a 50 MHz EM gain; (FIG. 10B) the CRI image showing no presence of atherosclerotic plaque, using edge detection software according to one embodiment; (FIG. 10C) a topographical image highlighting the distribution of the radioluminescence signal intensity using contour detection software according to one embodiment;

(FIG. 11A) a graph showing that an average of 400 A-lines were collected from the mouse left carotid artery of FIGS. 7A and 7B, using a PAT imaging system, according to one embodiment, where the CRI-PAT probe was placed in close proximity of 0.8 μm, and the laser was excited at 920 nm wavelength, using a 7 ns tunable pulsed laser at 20 Hz repetition rate; (FIG. 11B) a 3D PAT image superimposed on an ultrasound image that exhibited the presence of moderate level of lipid (2+), using software to reconstruct and superimpose the PAT image, according to one embodiment; and (FIG. 11C) a histology image of the left carotid artery, confirming the presence of moderate inflammation (2+), lipid (2+), and macrophages (2+), with 10% lumen occlusion and no presence of calcification (0+);

(FIG. 12A) CRI images of mice ligated left carotid artery showed 63× brighter radioluminescence signal at the atherosclerotic plaque area compared to non-ligated right carotid artery at 45 seconds exposure time; (FIG. 12B) verification IVIS-200 images of left carotid artery exhibited 65× brighter radioluminescence signal compared to negative-control right carotid artery; and (FIG. 12C) radioluminescence signal intensity of mice left carotid arteries showed a linear relationship with exposure time;

FIGS. 13A-13C are: (FIG. 13A) a photograph of a human carotid endarterectomy sample (i.e., atherosclerotic plaque removed from a carotid artery); (FIG. 13B) a CRI image of the same sample at 45 seconds exposure, binning 4×4, and EM Gain of 50 MHz as a control (before 18F-FDG was injected); and (FIG. 13C) a verification IVIS-200 image of the same sample after 18F-FDG was injected and placed under a scintillating screen at 45 seconds exposure time;

FIGS. 14A-14C are: (FIG. 14A) a CRI image of the sample of FIG. 13A, after 18F-FDG injection at 45 seconds exposure time with binning 1×1 and EM Gain of 50 MHz; (FIG. 14B) a CRI image of the sample of FIG. 13A, after application of edge detection software, according to one embodiment, to outline the location with the highest radioluminescence signal; and (FIG. 14C) a CRI image of the sample of FIG. 13A, after application of contour detection software, according to one embodiment, to highlight the distribution of the radioluminescence signal intensity;

FIGS. 15A-15C are: (FIG. 15A) a CRI image of the sample of FIG. 13A, after 18F-FDG injection at 45 seconds exposure with binning 4×4 and EM Gain of 50 MHz; (FIG. 15B) a CRI image of the sample of FIG. 13A, after application of edge detection software, according to one embodiment, to outline the location with the highest radioluminescence signal; and (FIG. 15C) a CRI image of the sample of FIG. 13A, after application of contour detection software, according to one embodiment, to highlight the distribution of the radioluminescence signal intensity;

FIGS. 16A-16C are: (FIG. 16A) a graph showing that an average of 400 A-lines were collected with our PAT system from the sample of FIG. 13A, when the CRI-PAT probe was placed in close proximity of 0.8 µm, and laser was excited at 920 nm wavelength using a 7 ns tunable pulsed laser at 20 Hz repetition rate; (FIG. 16B) a 3D PAT image the sample of FIG. 13A, superimposed on an ultrasound image, which exhibits the presence of severe lipid and cholesterol in the sample, using software to reconstruct and superimpose the PAT image, according to one embodiment; and (FIG. 11C) a histology image the sample of FIG. 13A, showing giant cells and cholesterol cleft, a representation of severe lipid and cholesterol, with moderate inflammation (2+), calcification (2+), and macrophages (2+) with 30% lumen occlusion;

FIGS. 17A-17C are graphs, illustrating data from CRI images of human samples, exhibiting: (FIG. 17A) carotid arteries 60×; (FIG. 17B) coronary arteries 53× and all human samples 58× brighter (not shown here) compared to control at 45 seconds exposure; and (FIG. 17C) radioluminescence signal intensity from human carotid and coronary arteries showed a linear relationship with exposure time; and FIGS. 18A-18C are graphs, illustrating verification images of human samples with IVIS-200 system, exhibiting: (FIG. 18A) carotid arteries 62×; (FIG. 18B) coronary arteries 56× brighter radioluminescence signal compared to control at 45 seconds exposure; and (FIG. 18C) radioluminescence signal intensity from all human carotid and coronary arteries showed a linear relationship with exposure time.

DETAILED DESCRIPTION

As mentioned above, this disclosure describes a dual-modality, scintillator catheter probe. The term "dual-modality" refers to the two imaging modes of the probe—catheter radionuclide imaging ("CRI") and photoacoustic tomography ("PAT"). The probe, and the CRI-PAT imaging system of which it is a part, typically (but not necessarily) uses both imaging modalities to help a user evaluate atherosclerotic plaque. Although reference may be made herein to detecting atherosclerotic plaque in coronary arteries, the probe and method for using it may be used to detect atherosclerosis in any artery in a human or animal body, such as but not limited to carotid arteries, peripheral arteries and the like.

Vulnerable atherosclerotic plaque is composed of a thin fibrous cap, a large lipid pool, and a large number of macrophages. These macrophages uptake an increased amount of 18F-fluorodeoxyglucose (18F-FDG) glucose molecule, compared to normal arterial tissue. The probe device described herein is designed such that when the 18F-FDG enriched vulnerable plaque comes in contact with the probe, the decay from the FDG, especially the beta-particles, will cause a vibration in the scintillator of the probe and emit optical radiation in the visible range. This emitted light is captured with a sensitive camera of an optical system housed in the probe. This is the CRI modality. In this way, the probe can detect vulnerable atherosclerotic plaque with high sensitivity and accuracy, unlike currently available imaging modalities. The probe is also able to use the PAT modality to outline the location of a vulnerable atherosclerotic plaque and provide information pertaining to the diseased tissue constituents. When pulsed laser light illuminates tissue, the optical absorbers there (such as lipid, calcification) undergo thermoelastic expansion, generating an acoustic pressure wave, which is detected with an ultrasound transducer in the probe. This is the PAT modality.

Figure 1:
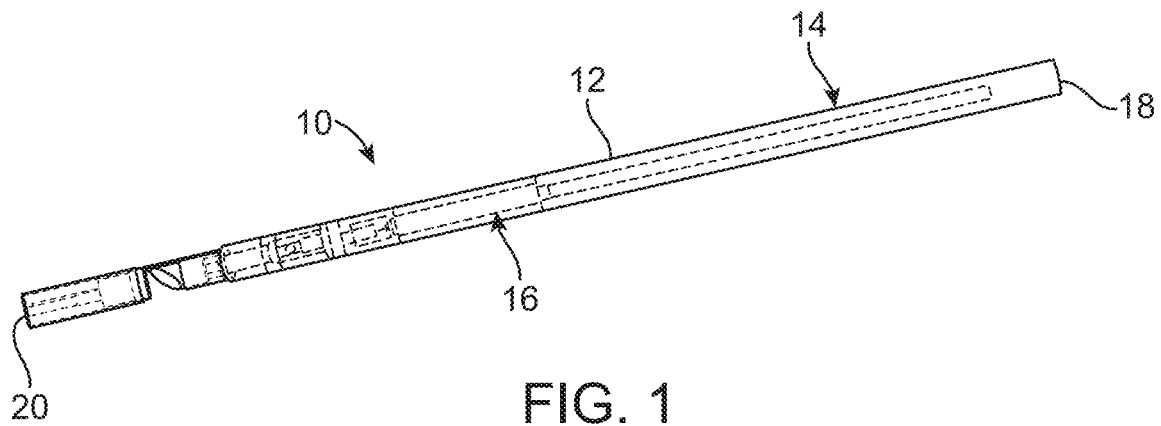
FIG. 1 is a side view of a dual-modality probe, according to one embodiment.

Referring now to FIG. 1, in one embodiment, a CRI-PAT scintillator probe 10 may include a tubular outer shaft 12 or housing, having a distal end 18 (or "front end") and a proximal end 20 (or back end"). In this embodiment, outer shaft 12 includes multiple different shaft (or "tube") components, such as a motor outer tube 14, which are illustrated in greater detail in relation to FIG. 2. In alternative embodiments, however, outer shaft 12 may have a different configuration and may include fewer or a greater number of parts. For example, in one embodiment outer shaft 12 may be one, continuous structure. Motor outer tube 14 may be made of stainless steel or any other suitable, medical grade metal or polymer, according to various embodiments. Similarly, other parts of outer shaft 12 and other shaft/tube components may be made out of stainless steel, or any other suitable, medical grade metal(s) or polymer(s).

As illustrated in FIG. 1, probe 10 may also include a motor inner tube 16. In this embodiment, motor outer tube 14 has an inner diameter (ID) of 0.135", an outer diameter (OD) of 0.148", and a length of 3.5". Motor inner tube 16 has an inner diameter of 0.0808", an outer diameter of 0.134" and a length of 0.511". These are only one set of exemplary measurements of these components, however. Distal end 18 of shaft 12 is the end that is advanced the farthest into the patient and thus represents the front end of probe 10. Proximal end 20 is typically configured for attachment to a flexible catheter, so that probe 10 can be advanced through a femoral artery or other access artery and eventually into a carotid artery. As such, proximal end 20 may be configured to simply be inserted into a distal end of a catheter device, or it may alternatively include one or more attachment features for attaching to a catheter.

Figure 2:
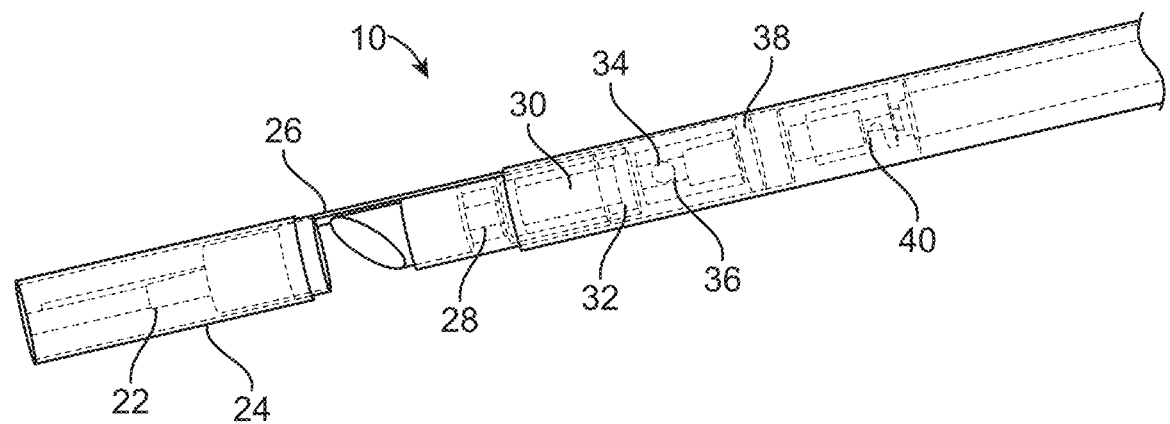
FIG. 2 is a close-up, side view of a proximal portion of the probe of FIG. 1, with a scintillating window removed.

Referring now to FIG. 2, probe 10 may include a number of different tubes, housings, shafts and/or couplers, for holding, housing and/or connecting various parts of probe 10. Again, probe 10 may include different combinations, sizes and/or numbers of components in alternative embodiments, without departing from the scope of the present invention. In the illustrated embodiment, probe 10 includes and imaging bundle grin tube 22 (0.042" ID, 0.045" OD), a transducer outer tube 24 (0.135" ID, 0.148" OD, 0.5" length), a bridge tube 26 (0.125" ID, 0.134" OD, 0.5" length), a mirror coupler 28 (0.041" ID, 0.0937" OD, 0.060" length), a jewel bearing spacer tube 30 (0.054" ID, 0.068" OD, 0.17" length), a jewel bearing tube 32 (0.100" ID, 0.134" OD, 0.23" length), a mirror shaft 34 (0.040" OD, 0.39" length), a mirror magnet housing 36 (0.041" ID, 0.0937" OD, 0.18" length), a window spacer tube 38 (0.125" ID, 0.134" OD, 0.025" length), and a motor magnet housing 40 (0.024" ID, 0.0937" OD, 0.15" length).

Figure 3:
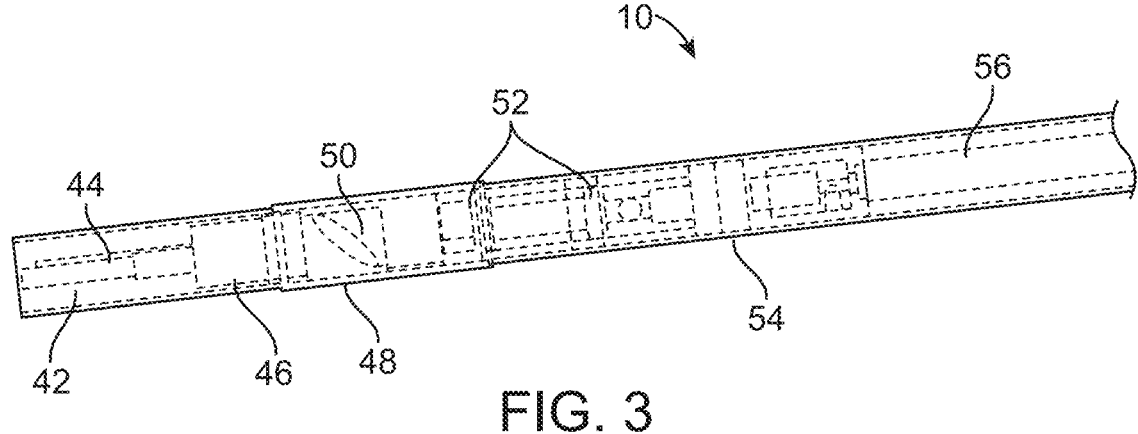
FIG. 3 is a close-up, side view of the proximal portion of the probe of FIGS. 1 and 2, with the scintillating window in place.

Referring now to FIG. 3, probe 10 may further include a number of internal features, which are housed within or otherwise coupled to the tubes, housings, shafts, etc., described above in relation to FIG. 2. As mentioned above, various alternative embodiments may include different numbers, shapes, types and/or sizes of internal features, without departing from the scope of the invention. In the illustrated embodiment, probe 10 includes a leached imaging bundle 42 (or "OF-2 imaging fiber bundle", 1.17 mm diameter, 0.9 mm imaging area), a light guiding optical fiber 44 (or "OF-1 optical fiber", for example, a multimode fiber having a 0.22 NA, 200 μm core diameter), a single-element ultrasonic transducer 46 (for example, a Lithium Niobate LNO, 40 MHz, unfocused, ring transducer with OD 3.0988 mm, ID 1.37 mm, and length 5.1054 mm (0.122" OD, 0.2009" length)), a scintillating imaging window 48 (0.137" ID, 0.147" OD, 0.39" length), a 45-degree mirror 50 (0.1181" OD, 0.2362" length), a jewel bearing 52 (0.0405" ID, 0.098" OD, 0.0301" length), a window 54 (0.134" OD, 0.05" length), and a mechanical micro-motor 56 (or "gear motor", 0.0787" OD, 0.5" length).

Single-element ultrasonic transducer 46 may be used for high Signal to Noise Ratio (SNR), and its relatively slow speed may be compensated for with a MHz repetition rate laser. Laser pulses from a portable UV-VIS-NIR tunable laser (7 ns pulse length with 20 Hz repetition rate) will be guided by light guiding OF-1 optical fiber 44, which is parallel to OF-2 imaging fiber-bundle 42. Leached imaging bundle 42 and multimode fiber 44 may extend through a central hole in transducer 46 (1.37 mm diameter in one embodiment). The proximal end of OF-2 leached imaging fiber-bundle 42 may be a 1 mm diameter Grin lens, with a working distance of 5 mm, paraxial magnification 5.86, NA:0.5, and refractive index: 1.635.

In use, probe 10 may be used for circumferential sector scanning (beta-particle scanning), by rotating 45-degree concave mirror 50 (3 mm diameter, protected aluminum on glass substrate, with the reflection surface at 45° to the probe's axis, according to one embodiment. Mirror 50 may be driven by geared micro-motor 56 (2.0 mm OD, 18.62 mm length, gear ratio 254:1, according to one embodiment), to steer a light beam from optical fibers 42, 44 toward the tissue being imaged and an acoustic wave from the tissue to transducer 46. Because water and glass have a large ratio of sound propagation speeds (longitudinal wave:1.5/5.1, shear wave:1.5/3.3), scanning mirror 50 may exhibit total external reflection within the acceptance angles of ultrasonic transducer 46 and may insert no additional propagation losses into the ultrasonic detection. Scanning mirror 50 replaces the conventional flexible shaft-based mechanical scanning, enabling circumferential beta-particle scanning, without moving other illumination optics or ultrasonic transducer 46.

Optical fibers 42, 44, the transducer's signal wires, and micro-motor wires may be encapsulated in a flexible catheter body, for example a flexible portion of, or addition to, outer tube 12, with an outer diameter of 3.2 mm, where 0.5 mm may be used for a catheter enclosure. Mirror's 50 rotational speed will typically be kept constant during use. To provide a matching medium for acoustic wave propagation, a housing space for ultrasound transducer 46 and scanning mirror 50 may be filled with deionized water and sealed with a scintillating imaging window 48, which in this embodiment is a 125 μm thick scintillating screen made from organic phosphors, such as CaF2(Eu) and anthracene mixed in polyvinyltolune. Micro-motor 56 may be isolated from the water by window 54, and the torque required for mirror rotation will transfer through a micro-magnetic (OD 1.58 mm with a length of 3.175 mm) coupling mechanism.

Figure 4C:
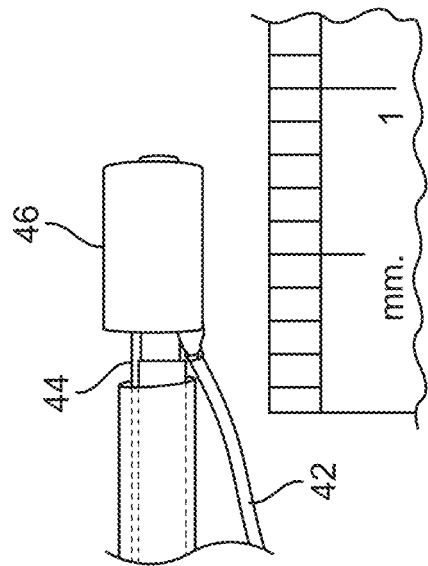
FIG. 4C is a side view of a portion of the probe of FIGS. 1-3, specifically a single element transducer holding a 18,000-pixel, leached image fiber and a 200 micrometer core multi-mode fiber.
Figure 4B:
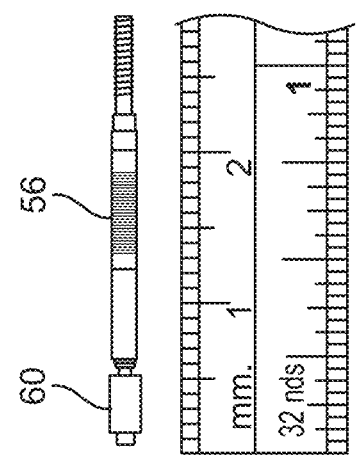
FIG. 4B is a side view of a portion of the probe of FIGS. 1-3, specifically a micro-motor connected to another micromagnet.
Figure 4A:
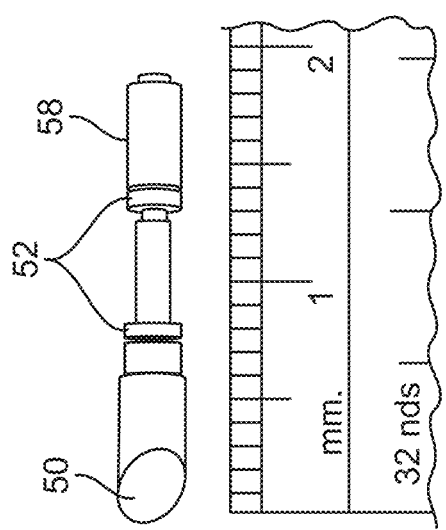
FIG. 4A is a side view of a portion of the probe of FIGS. 1-3, specifically a 45-degree mirror connected to a micromagnet and two jewel bearings for reducing friction during rotation.
Figure 4F:
FIG. 4F is a side view of a portion of the probe of FIGS. 1-3, specifically a spacer for preventing water flowing from the imaging window compartment to the micro-motor holding compartment.
Figure 4E:
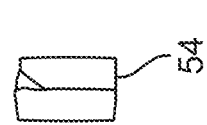
FIG. 4E is a side view of a portion of the probe of FIGS. 1-3, specifically a holder for the transducer and 45-degree mirror.
Figure 4D:
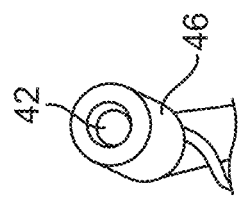
FIG. 4D is an end-on view of the transducer of FIG. 4C.

Referring now to FIGS. 4A-4E, various components of probe 10 are illustrated as disassembled parts. FIG. 4A is a side view of a portion of probe 10 including 45-degree mirror 50 connected to a micro-magnet 58 and two jewel bearings 52 for reducing friction during mirror rotation. FIG. 4B is a side view of a portion of probe 10, including micro-motor 56 connected to another micro-magnet 60. FIG. 4C is a side view of a portion of probe 10, including single element transducer 46, holding 18,000-pixel leached image fiber 42 and 200 micrometer core multi-mode fiber 44. FIG. 4D is an end-on view of transducer 46. FIG. 4E is a side view bridge tube 26 from FIG. 2, which acts as a holder for transducer 46 and 45-degree mirror 50. FIG. 4F is a side view of window 54 from FIG. 3, which acts as a spacer for preventing water from flowing from the imaging window compartment to the micro-motor holding compartment.

Referring now to FIGS. 5A-5C, a portion of probe 10 is illustrated during use. FIG. 5A shows scintillating window 48. FIG. 5B shows scintillating window 48 and 45-degree mirror 50, with tunable laser light 62 being delivered through the water-coupled scintillating window 48 at 540 and 560 nm wavelength (green band). FIG. 5C shows scintillating window 48 and 45-degree mirror 50, with tunable laser light 62 being delivered through the water-coupled scintillating window 48 at 1180, 1210, and 1235 nm wavelength (blue band).

Figure 6:
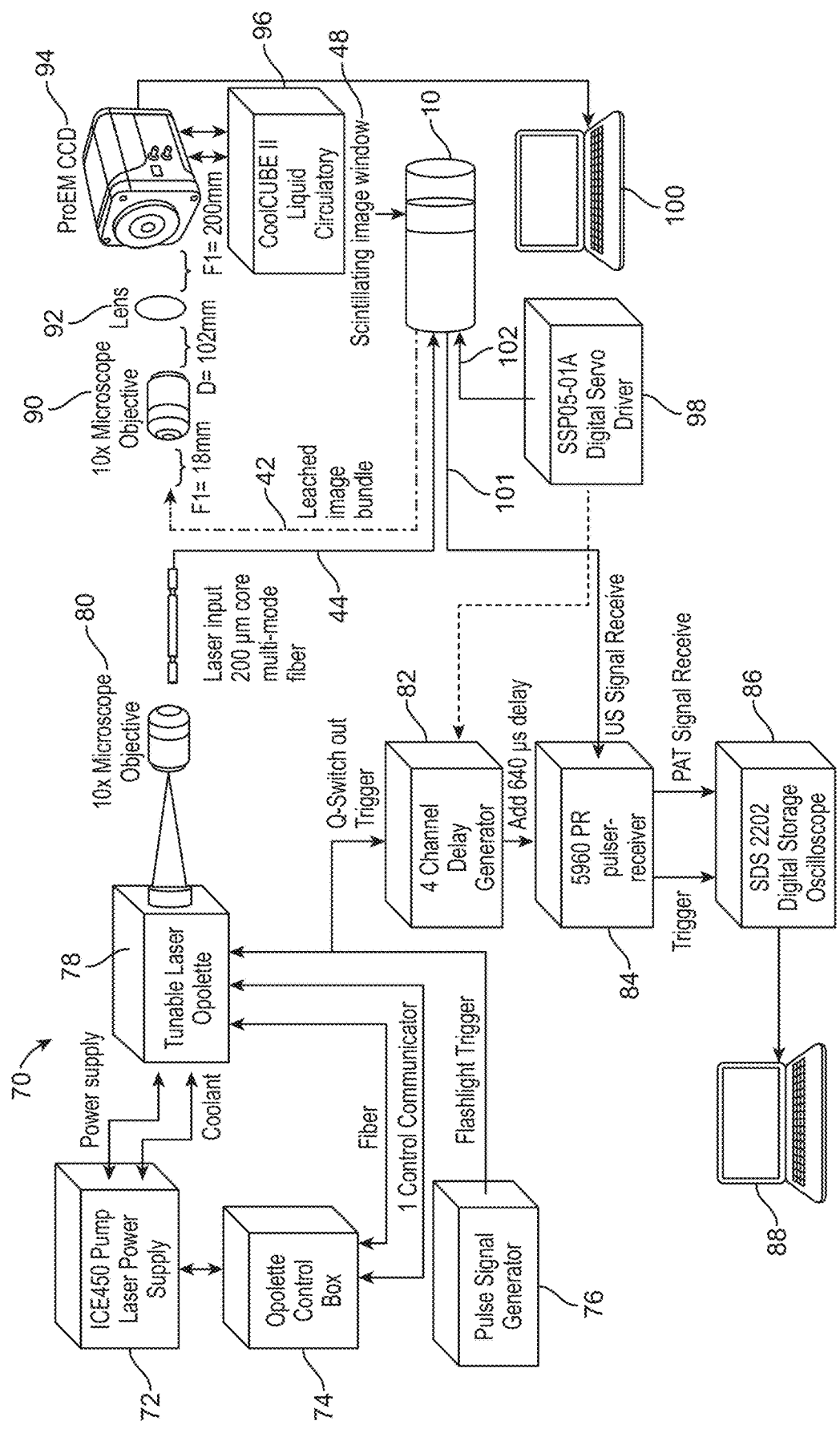
FIG. 6 is a diagrammatic flow chart of a CRI-PAT imaging system, illustrating flow of light, information, etc., between the various components of the system, according to one embodiment.

Referring to FIG. 6, a CRI-PAT imaging system 70, according to one embodiment, is illustrated. Again, system 70, in various alternative embodiments, may include additional components, fewer components, different types, shapes, sizes or configurations of components, different combinations, and the like. In this embodiment, system 70 includes probe 10, which as described above includes scintillating window 48, leached image bundle 42 and multimode fiber 44, among other components. System 70 may also include any or all of the following: a laser power supply 72 (such as an ICE450 pump), a control box 74 (e.g., Opolette), a pulse signal generator 76, a tunable laser 78 (e.g., Opolette), two 10× microscope objectives 80, 90, a 4-channel delay generator 82, a pulser-receiver 84 (e.g., 5960 PR), a digital storage oscilloscope (e.g., SDS 2202), two laptop computers 88, 100 or other computing devices, a lens 92, a CCD camera 94 (e.g., ProEM CCD), a liquid circulator 96 (e.g., CoolCUBE II), and a digital servo-driver 98 (e.g., SSP05-01A). These components may be connected via any suitable connectors, as illustrated in FIG. 6. Leached image bundle 42 and multi-mode fiber 44 may represent two wires that enter the proximal end of probe 10. In some embodiments, two additional wires 101, 102 may connect pulser-receiver 84 and digital servo-driver 98 to probe 10, so that four wires total may connect probe 10 to system 70. Other embodiments may include fewer or greater numbers of wires.

To use CRI-PAT probe 10 and system 70, for example to detect and evaluate an atherosclerotic plaque in a coronary artery, first the patient is intravenously injected with 18F-FDG, into the artery of interest. Probe 10 is then advanced, for example through a femoral artery cut-down, into the coronary artery being examined, for example via a femoral artery access location or other suitable location. In some embodiments, there may be a waiting period between injecting the 18F-FDG and inserting probe 10 into the patient. For example, the waiting period may be anywhere from several minutes to several hours, but at least in some embodiments it may be approximately one to two hours.

Once probe 10 is positioned in an artery to be examined, the user will typically first use the CRI modality of probe 10 to locate vulnerable plaque in the artery. Macrophages from the vulnerable plaque uptake increased amounts of 18F-FDG glucose molecule compared to normal arterial tissue. When the 18F-FDG enriched vulnerable plaque comes in contact with probe 10, beta-particles emitted from the 18F-FDG will cause a vibration in the scintillator of probe 10 and will thus emit optical radiation in visible range. This optical radiation is captured with the highly sensitive camera of imaging system 70, with a very high signal-to-noise ratio. In this fashion, the CRI modality of probe 10 is used to locate the vulnerable plaque.

The PAT modality of probe 10 may then be used to collect further data regarding the vulnerable plaque. In this modality, probe 10 is used to shine laser light circumferentially around the inner wall of the artery, using spinning mirror 50. Optical absorbing constituents in the arterial wall, such as lipid and calcification, undergo thermoelastic expansion, generating an acoustic pressure wave, which is detected with ultrasound transducer 46 in probe 10. The detected acoustic pressure wave can then be used to provide data as to the constituents of the vulnerable atherosclerotic plaque.

Experimental Results

In one experiment, 18F-FDG was IV injected into an in vivo mouse one hour before a mouse heart with attached left and right carotid arteries was removed. The left carotid was ligated, and the right carotid was used as a control. 18F-FDG was injected, and the left and right carotid arteries were imaged, using the CRI-PAT probe and system described herein. A description of the figures follows immediately below.

FIGS. 7A and 7B are: (FIG. 7A) an image of ex vivo murine carotid arteries, one hour after 18F-FDG IV injection of 200 where ligated left and non-ligated right carotid (negative control) arteries are still attached to the heart (positive control), immediately after the organ was harvested for imaging; and (FIG. 7B) radioluminescence signal verification with IVIS-200 imaging system to illustrate the glucose uptake by macrophages in atherosclerotic plaque.

FIGS. 8A-8C are: (FIG. 8A) a CRI image of the ligated left carotid artery of FIGS. 7A and 7B, showing a high radioluminescence signal at the atherosclerotic plaque (exposure time was 45 seconds with binning 1×1 at 50 MHz EM gain); (FIG. 8B) the CRI image showing an outline of the atherosclerotic plaque, using edge detection software according to one embodiment; and (FIG. 8C) a topographical image highlighting the distribution of the radioluminescence signal intensity using contour detection software according to one embodiment.

FIGS. 9A-9C are: (FIG. 9A) a CRI image of the same ligated left carotid artery of FIGS. 7A and 7B, showing a high radioluminescence signal at the atherosclerotic plaque (exposure time was 45 seconds with binning 4×4 at 50 MHz EM gain); (FIG. 9B) the CRI image showing an outline of the atherosclerotic plaque, using edge detection software according to one embodiment; and (FIG. 9C) a topographical image highlighting the distribution of the radioluminescence signal intensity using contour detection software according to one embodiment.

FIGS. 10A-10C are: (FIG. 10A) a CRI image of the same right carotid artery of FIGS. 7A and 7B, where exposure time was 45 seconds with binning 4×4 a 50 MHz EM gain; (FIG. 10B) the CRI image showing no presence of atherosclerotic plaque, using edge detection software according to one embodiment; (FIG. 10C) a topographical image highlighting the distribution of the radioluminescence signal intensity using contour detection software according to one embodiment.

Figure 11A:
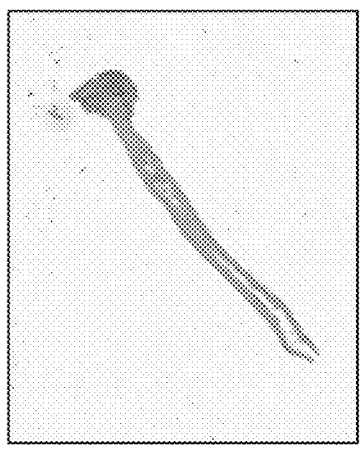
FIGS. 11A-11C are.
Figure 11B:
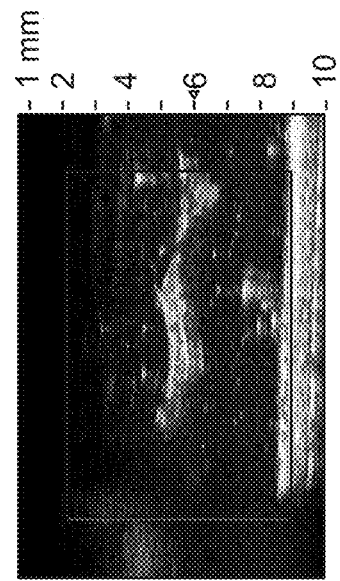
Figure 11C:
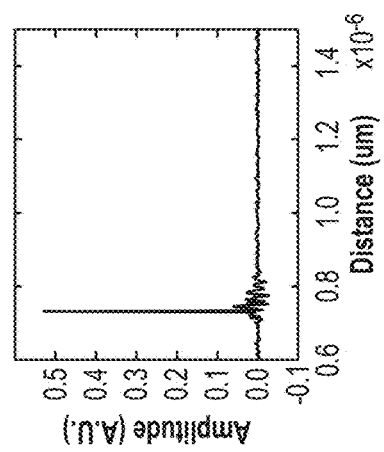

FIGS. 11A-11C are: (FIG. 11A) a graph showing that an average of 400 A-lines were collected from the mouse carotid artery of FIGS. 7A and 7B, using a PAT imaging system, according to one embodiment, where the CRI-PAT probe was placed in close proximity of 0.8 μm, and the laser was excited at 920 nm wavelength, using a 7 ns tunable pulsed laser at 20 Hz repetition rate; (FIG. 11B) a 3D PAT image superimposed on an ultrasound image that exhibited the presence of moderate level of lipid (2+), using software to reconstruct and superimpose the PAT image, according to one embodiment; and (FIG. 11C) a histology image of the left carotid artery, confirming the presence of moderate inflammation (2+), lipid (2+), and macrophages (2+), with 10% lumen occlusion and no presence of calcification (0+).

Figure 12A:
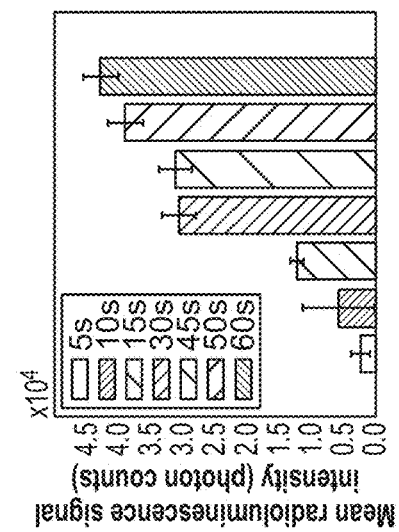
FIGS. 12A-12C are graphs, illustrating.
Figure 12B:
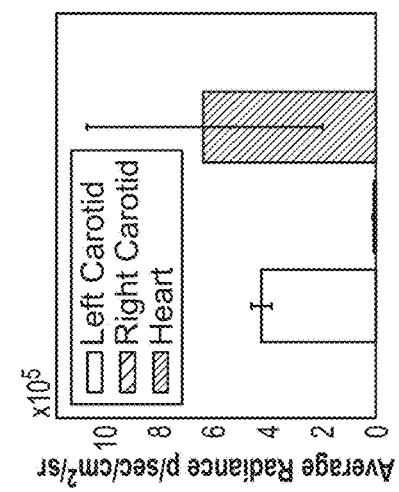
Figure 12C:
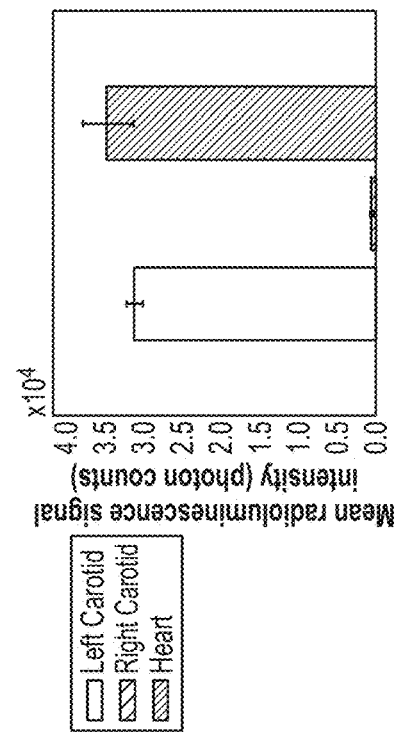

FIGS. 12A-12C are graphs, illustrating: (FIG. 12A) CRI images of mice ligated left carotid artery showed 63× brighter radioluminescence signal at the atherosclerotic plaque area compared to non-ligated right carotid artery at 45 s exposure time; (FIG. 12B) verification IVIS-200 images of left carotid artery exhibited 65× brighter radioluminescence signal compared to negative-control right carotid artery; and (FIG. 12C) radioluminescence signal intensity of mice left carotid arteries showed a linear relationship with exposure time.

In another experiment, a human carotid endarterectomy sample was analyzed, using the CRI-PAT probe and imaging system described herein. The endarterectomy sample was atherosclerotic plaque tissue, removed from a human carotid artery and injected with $^{18}$F-FDG ex vivo.

FIGS. 13A-13C are: (FIG. 13A) a photograph of the human carotid endarterectomy sample (i.e., atherosclerotic plaque removed from an artery); (FIG. 13B) a CRI image of the same sample at 45 seconds exposure, binning 4×4, and EM Gain of 50 MHz as a control (before 18F-FDG was injected); and (FIG. 13C) a IVIS-200 image of the same sample after 18F-FDG was injected and placed under a scintillating screen at 45 seconds exposure time.

FIGS. 14A-14C are: (FIG. 14A) a CRI image of the sample of FIG. 13A, after 18F-FDG injection at 45 seconds exposure time with binning 1×1 and EM Gain of 50 MHz; (FIG. 14B) a CRI image of the sample of FIG. 13A, after application of edge detection software, according to one embodiment, to outline the location with the highest radioluminescence signal; and (FIG. 14C) a CRI image of the sample of FIG. 13A, after application of contour detection software, according to one embodiment, to highlight the distribution of the radioluminescence signal intensity.

FIGS. 15A-15C are: (FIG. 15A) a CRI image of the sample of FIG. 13A, after 18F-FDG injection at 45 seconds exposure with binning 4×4 and EM Gain of 50 MHz; (FIG. 15B) a CRI image of the sample of FIG. 13A, after application of edge detection software, according to one embodiment, to outline the location with the highest radioluminescence signal; and (FIG. 15C) a CRI image of the sample of FIG. 13A, after application of contour detection software, according to one embodiment, to highlight the distribution of the radioluminescence signal intensity.

FIGS. 16A-16C are: (FIG. 16A) a graph showing that an average of 400 A-lines were collected with our PAT system from the sample of FIG. 13A, when the CRI-PAT probe was placed in close proximity of 0.8 μm, and laser was excited at 920 nm wavelength using a 7 ns tunable pulsed laser at 20 Hz repetition rate; (FIG. 16B) a 3D PAT image the sample of FIG. 13A, superimposed on an ultrasound image, which exhibits the presence of severe lipid and cholesterol in the sample, using software to reconstruct and superimpose the PAT image, according to one embodiment; and (FIG. 16C) a histology image the sample of FIG. 13A, showing giant cells and cholesterol cleft, a representation of severe lipid and cholesterol, with moderate inflammation (2+), calcification (2+), and macrophages (2+) with 30% lumen occlusion.

FIGS. 17A-17C are graphs, illustrating data from CRI images of human samples, exhibiting: (FIG. 17A) carotid arteries 60×; (FIG. 17B) coronary arteries 53× and all human samples 58× brighter (not shown here) compared to control at 45 seconds exposure; and (FIG. 17C) radioluminescence signal intensity from human carotid and coronary arteries showed a linear relationship with exposure time.

FIGS. 18A-18C are graphs, illustrating verification images of human samples with IVIS-200 system, exhibiting: (FIG. 18A) carotid arteries 62×; (FIG. 18B) coronary arteries 56× brighter radioluminescence signal compared to control at 45 seconds exposure; and (FIG. 18C) radioluminescence signal intensity from all human carotid and coronary arteries showed a linear relationship with exposure time.

Although this application includes a complete and accurate description of various aspects and embodiments of a probe device, system and method for detecting and evaluating atherosclerotic plaque, any suitable changes may be made to any of the embodiments described herein, without departing from the scope of the invention. For example, various alternative embodiments of the described CRI-PAT imaging probe or system may include fewer, greater or different components, or the described components may be arranged in a different way, without departing from the scope. Similarly, the described method may be performed with fewer, greater or different steps, or the step may be performed in a different order, without departing from the scope. Therefore, the above description is provided for exemplary purposes only and should not be interpreted as limiting the scope of the invention as defined by the claims.

What is claimed is:

1. A probe device for detecting atherosclerotic plaque in an artery, the device comprising:
    an elongate hollow shaft, having a proximal end for coupling with a catheter and a distal end;
    an opening in a side of the shaft;
    a scintillating window disposed over the opening to form a watertight seal and thus form an imaging window compartment in the shaft;
    a 45-degree rotating mirror disposed at least partially within the imaging window compartment in the shaft;
    an ultrasound transducer disposed at least partially within the imaging window compartment in the shaft;
    a leached imaging bundle extending through a central bore of the ultrasound transducer;
    a multimode fiber extending through the central bore of the ultrasound transducer;
    a mechanical micro-motor extending through the shaft and coupled with the rotating mirror; and
    at least one micro-magnet connecting the micro-motor with the rotating mirror.

2. The probe device of claim 1, further comprising a spacer for preventing water from flowing from the imaging window compartment to a micro-motor holding compartment in the shaft where the micro-motor is located.

3. The probe device of claim 1, wherein the leached imaging bundle comprises an 18,000-pixel leached image fiber.

4. The probe device of claim 1, further comprising deionized water disposed within the imaging window compartment.

5. The probe device of claim 1, wherein the probe device comprises a catheter radionuclide imaging and photoacoustic tomography (CRI-PAT) probe.

6. A system for detecting atherosclerotic plaque in an artery, the system comprising:
    a catheter radionuclide imaging and photoacoustic tomography (CRI-PAT) probe, comprising;
        an elongate hollow shaft, having a proximal end for coupling with a catheter and a distal end;
        an opening in a side of the shaft;
        a scintillating window disposed over the opening to form a watertight seal and thus form an imaging window compartment in the shaft;
        a 45-degree rotating mirror disposed at least partially within the imaging window compartment in the shaft; and
        an ultrasound transducer disposed at least partially within the imaging window compartment in the shaft;
        a leached imaging bundle extending through a central bore of the ultrasound transducer;
        a multimode fiber extending through the central bore of the ultrasound transducer;
        a mechanical micro-motor extending through the shaft and coupled with the rotating mirror; and
        at least one micro-magnet connecting the micro-motor with the rotating mirror; and
    at least one component coupled with the CRI-PAT probe and configured to provide power to at least one of a catheter radionuclide modality or a photoacoustic tomography modality of the CRI-PAT probe.

7. The system of claim 6, wherein the at least one component is selected from the group consisting of a laser power supply, a control box, a pulse signal generator, a tunable laser, a microscope objective, a 4-channel delay generator, a pulser-receiver, a digital storage oscilloscope, a computer, a lens, a CCD camera, a liquid circulator and a digital servo-driver.

8. A method for detecting atherosclerotic plaque in an artery, the method comprising:
    injecting 18F-fluorodeoxyglucose (18F-FDG) into the artery;
    advancing a catheter radionuclide imaging and photoacoustic tomography (CRI-PAT) probe into the artery;
    detecting optical radiation from the atherosclerotic plaque through a scintillating window on the CRI-PAT probe, with one or more optical fibers in the CRI-PAT probe;
    emitting laser light circumferentially around an inner wall of the artery with a laser and a 45-degree rotating mirror in the CRI-PAT probe; and
    detecting an acoustic pressure wave from the atherosclerotic plaque in response to the emitted laser light, using an ultrasound transducer located inside the scintillating window of the CRI-PAT probe.

9. The method of claim 8, further comprising identifying the atherosclerotic plaque as a vulnerable plaque, using the detected optical radiation from the atherosclerotic plaque.

10. The method of claim 8, further comprising identifying multiple constituents of the atherosclerotic plaque, based on the detected acoustic pressure wave.

11. The method of claim 8, further comprising providing a first image of the atherosclerotic plaque.

12. The method of claim 11, wherein providing the first image comprises superimposing the first image on a second image of an artery in which the atherosclerotic plaque resides.

13. The method of claim 12, wherein the second image of the artery comprises an ultrasound image.

14. The method of claim 8, wherein emitting the laser light comprises directing the light circumferentially with a spinning mirror in the CRI-PAT probe.

15. The method of claim 14, wherein emitting the laser light comprises emitting pulsed laser light.

* * * * *